(12) United States Patent
Gazza

(10) Patent No.: US 8,172,844 B2
(45) Date of Patent: May 8, 2012

(54) BONE IMPLANT DEVICE

(75) Inventor: Gianluca Gazza, Monaco (MC)

(73) Assignee: Nobil Bio Ricerche S.R.L., Villafranca D'Asti (IT)

( * ) Notice: Subject to any disclaimer, the term of this patent is extended or adjusted under 35 U.S.C. 154(b) by 860 days.

(21) Appl. No.: 11/664,838

(22) PCT Filed: Oct. 6, 2004

(86) PCT No.: PCT/IB2004/003260
§ 371 (c)(1),
(2), (4) Date: Nov. 21, 2007

(87) PCT Pub. No.: WO2006/038056
PCT Pub. Date: Apr. 13, 2006

(65) Prior Publication Data
US 2008/0188938 A1    Aug. 7, 2008

(51) Int. Cl.
*A61B 17/56* (2006.01)
*A61B 17/58* (2006.01)
*A61F 2/30* (2006.01)

(52) U.S. Cl. .................................. 606/76; 606/907

(58) Field of Classification Search .............. 606/76–77, 606/231, 298, 331, 907–908, 910
See application file for complete search history.

(56) References Cited

U.S. PATENT DOCUMENTS

| | | | |
|---|---|---|---|
| 4,720,512 A | 1/1988 | Hu et al. | |
| 5,645,592 A * | 7/1997 | Nicolais et al. | 606/63 |
| 5,759,205 A | 6/1998 | Valentini | |
| 2004/0143180 A1 | 7/2004 | Zhong et al. | |
| 2006/0165962 A1 * | 7/2006 | Borck et al. | 428/195.1 |

FOREIGN PATENT DOCUMENTS

| | | |
|---|---|---|
| DE | 102 23 310 A1 | 12/2003 |
| WO | WO 00/56377 A1 | 9/2000 |

OTHER PUBLICATIONS

International Search Report dated Jul. 26, 2005 for International Patent Application No. PCT/IB2004/003260.

* cited by examiner

*Primary Examiner* — Thomas C. Barrett
*Assistant Examiner* — Sameh Boles
(74) *Attorney, Agent, or Firm* — Hogan Lovells US LLP

(57) ABSTRACT

The present invention relates to a bone implant device, particularly for dental and orthopedic prosthesis on the vertebral column, having a quicker osteo-integration compared to the prior art devices. Particularly, the present invention relates to an implant device, of metal or polymer nature, a layer of hyaluronic acid being chemically bound on the surface thereof, for use in applications in contact with the bone, with activity of stimulating the bone tissue growth, as well as a process for preparing the same.

20 Claims, 1 Drawing Sheet

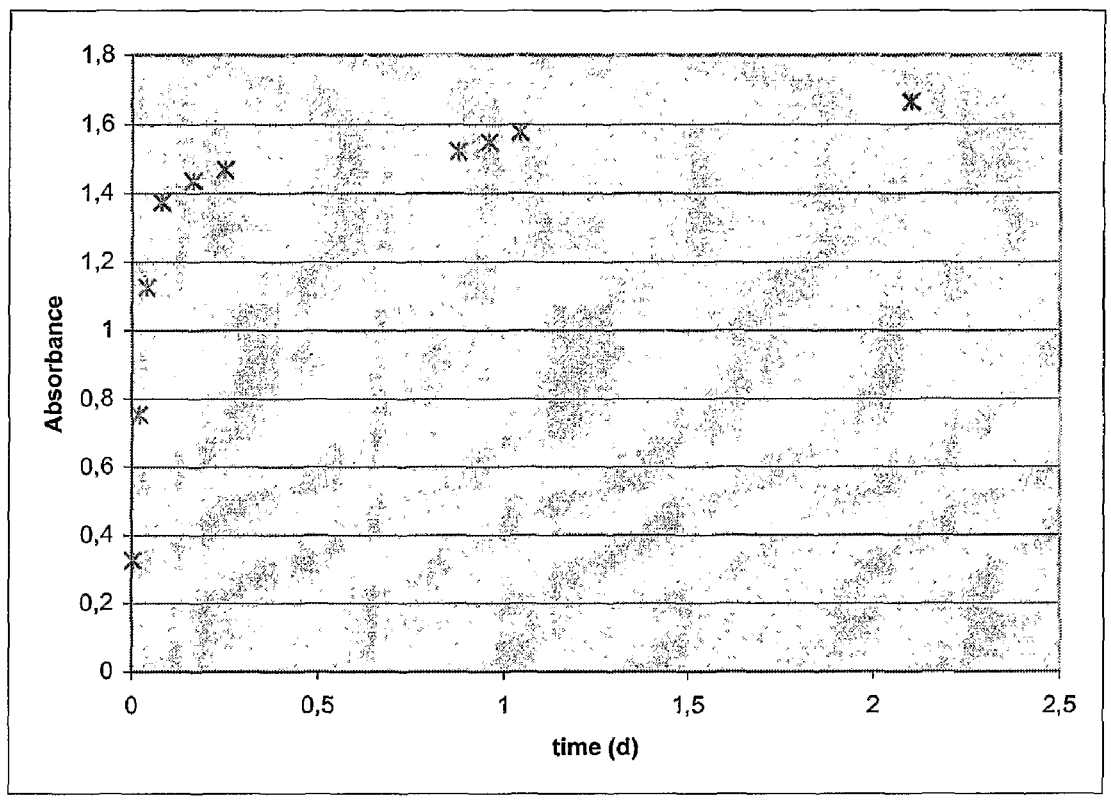

BONE IMPLANT DEVICE

The present invention relates to a bone implant device, particularly for dental prosthesis and orthopedic prosthesis in the vertebral column, providing a quicker osteo-integration than the prior art devices.

BACKGROUND OF THE INVENTION

The use of metal devices permanently implantable in bone tissue is widespread in various branches of medicine. For example, the dental implant surgery provides the use of screws, generally made of titanium, in the lower jaw or maxilla bones to artificially replace lost or no longer functional bone roots. In orthopedics, several devices for fracture fixation, reduction of vertebral mobility, vertebral column surgery, are commonly implanted in bone tissue.

In these applications, the implanted device is firmly locked in the implant site due to the growth, until direct contact with the device, of newly formed bone tissue. This phenomenon, which is known as the osteo-integration, has been widely studied and described in the technical-scientific literature of the sector, particularly as refers to the bone implant surgery by means of titanium devices. Contrarily to other processes of implantation of foreign material in tissues, entailing the encapsulation in a fibrous material, i.e fiber integration, the growth of bone tissue directly in contact with the device offers a firm anchorage, which makes the device suitable to withstand loads and perform structural tasks.

While the disciplines based on osteo-integration are recently having great success and ever-increasing applications, several problems still remain to be solved. Particularly, it is important to accelerate the osteo-integration process as much as possible, thereby reducing the time between the insertion of the implant and the actual load thereon. For example, in dentistry the implant is generally not "loaded", thereby the patient cannot perform his masticatory function by means of that implant, for a period of time ranging from 1 to 4 months after the intervention, in order to allow bone tissue healing and induce osteo-integration. Furthermore, while bones normally heal well with healthy and young people, it is often very slow with old and osteoporotic people, i.e. those more likely to require these interventions and being a significant portion of patients requiring implant operations for trauma or fixation of spine mobility.

As it is generally known that the surface properties of the implant devices play a basic role in the tissue response to the implant, a great number of researches has been carried out to improve the osteo-integration process by modifying the surface of the implantable devices. A detailed picture of these researches is set forth in "The bone-biomaterial interface" by Puleo and Nancy, Biomaterials 1999; 20:2311-2321, or the textbook Bone Engineering, Davies, published by EM SQUARED, Toronto, 2000. From studying these books and evaluating the devices being marketed, it is understood that the improvement of the surface properties is often pursued by means of surface roughening, for example by means of sandblasting, plasma-spray deposition or treatments with acids. The deposition of layers of ceramic materials with high bone affinity, such as the hydroxyapatite or the so-called bioglass, has also been studied and applied.

In addition to these methods, great interest has arisen in introducing on the surface of the implant devices biological molecules capable of promoting bone growth. Among the most studied molecules, there has been reported that the collagen, when immobilized to the surface of an implant titanium screw, can increase the osteo-integration speed. Particular peptides, i.e. small molecular fragments composing proteinic molecules, which are capable of interacting particularly with bone cells, have also proved effective when tested in vivo. To the purpose, the above-mentioned article by Puleo and Nancy studies the several molecules used for carrying out the biochemical modification of implant surfaces.

Though the biochemical modification of implant surfaces is a sector of great scientific and speculative interest, its practical application still has considerable problems. The collagen, for example, has problems of contamination as it originates from dubious animal sources (particularly, bovine collagen) or rejection due to possible incompatibility reactions among different species. The above-mentioned peptides are rather costly and poorly stable from a chemical point of view, such that resorting to the typical procedures of the sector, for example the sterilization, in the treatment of implant surfaces is hardly feasible.

The hyaluronic acid is a glycosaminoglycan diffused in all tissues of living beings, without any variation among species. It has very interesting biochemical and hydration characteristics and for this reason it is widely studied and used in various specialties within the biomedical field. An exhaustive overview of the application of the latter is set forth, for example, in some works containing the proceedings from the main conferences on hyaluronic acid: "The Biology of Hyaluronan", D. Evered and J. Whelan, Eds. Wiley, Chichester, 1989, "The Chemistry, Biology and Medical Applications of Hyaluronan and its Derivatives", T. C Laurent, Ed., Portland Press Ltd, London, 1998, "Redefining Hyaluronan", G. Abatangelo and P. H. Weigel, (Eds.), Elsevier, Amsterdam, 2000, "Hyaluronan", J. F. Kennedy, G. O. Phillips, P. A. Williams, V. Hascall, Eds., Woddhead Publishing Limited, 2002.

The hyaluronic acid, as a molecule in the homogeneous phase, plays an active role in the bone formation process, such as described, for example, by Bernard et al. in the above-mentioned work "Redefining Hyaluronan", G. Abatangelo and P. H. Weigel, (Eds.), Elsevier, Amsterdam, 2000, p. 215.

For this reason, hyaluronic acid-based gels imbibed of bone morphogenetic proteins or growth factors, have been successfully used in bone stimulation tests. Furthermore, it has been demonstrated that hyaluronic acid solutions, optionally coupled with the dexamethasone drug having osteogenic properties, exert a positive effect on the specialization in bone cells of marrow stromal cells, such as described by Zou et al., Biomaterials, 2004; 5375-5385, 25.

However, the interesting osteogenic potentiality of the hyaluronic acid, either as a gel or in solution, or the hyaluronic acid present in tissues cannot be immediately used in the bone tissue implantation devices as described above. In fact, the hyaluronic acid is very soluble in aqueous solutions and its time of permanence in situ is very short. Chemical techniques favouring the permanence of the hyaluronic acid in the implant site, such as cross-linking, chemical modification or surface immobilization, can alter the structure and molecular conformation of the hyaluronic acid and negatively affect the receptor-ligand specific interactions, thereby compromising the bioactive behaviour of the molecule. In fact, the bioactive properties of the hyaluronic acid derive from its capacity of interacting with specific receptors located on the cell wall, such as CD44 or RHAMM. Such as described by J. Lesley et al., J Biol. Chem. 2000 Sep. 1; 275(35):26967-75, this type of interaction is highly co-operative and, in order to be effective, requires the simultaneous interaction of many repeats of hyaluronic acid with a single receptor. The co-operative nature of the interaction implies the typical mobility of molecules in solution, therefore the immobilization of hyaluronic acid on material surfaces, such as described by Morra and Cassinelli, Journal of Biomaterials Science, Polymer Edition, 1999; 10(10):1107-24, leads to surfaces that do not allow any cell adhesion due to the inability of establishing specific interactions being sufficiently strong. The reduced adhesion of cells or biomolecules to surfaces with immobilized hyaluronic acid is substantiated in various scientific literature articles and is used, as set forth by Witt at al., "Hyaluronan", J. F. Kennedy, G. O. Phillips, P. A. Williams, V. Hascall, Eds., Woddhead Publishing Limited, 2002, volume 2, p. 27, to reduce adhesion phenomena subsequent to surgical operations. The hyaluronic acid immobilization on metal substrates and devices has been reported by Pitt et al., in the article: "Attachment of hyaluronan to metallic surfaces", issued in Journal of Biomedical Materials Research, vol. 68, p. 95, 2004. In accordance with the general knowledge, such as described above, in the cited article the surfaces with immobilized hyaluronic acid thereon are designated as being "biopassive" or with poor cell adhesion. The Authors of the article point out how the poor biological adhesion imparted by the immobilized hyaluronic acid layer can be used to prevent non-specific adhesion; and how, in order to obtain a specific bio-adhesion effect, it is necessary to bind adhesion peptides to this non-adhesive matrix.

Essentially, it is generally acknowledged that hyaluronic acid layers immobilized on solid surfaces have characteristics of resistance to biological adhesion, which is contrary to what one would desire to obtain by means of the bioactive action of hyaluronic acid immobilized on implantation devices, wherein the specific cell adhesion of the implant to the bone tissue is crucial for osteo-integration.

It is further acknowledged that the bone neoformation process requires a mineralization step being promoted by calcium ions binding to the surface. As described by Bernard et al. in the above-mentioned work, the hyaluronic acid, in nature, has an active effect in this step, thereby significantly contributing to the calcification process. The hyaluronic acid carboxylate groups can, in fact, chelate or complex calcium ions by exerting a positive action on the mineralization process. However, the immobilization of hyaluronic acid on the surface of implant devices normally implies binding the hyaluronic acid carboxylic groups with aminic or hydroxyl functionalities present on the substrate, with the consequent loss, in the bound hyaluronic acid, of carboxylic groups being available for chelation with calcium ions. Accordingly, the immobilization of the hyaluronic acid on the surface of these devices by the known methods does not lead to any improvement in the osteo-integration process.

On the other hand, the present applicant has surprisingly found that hyaluronic acid immobilized on implant screws, in accordance to what is set forth in the annexed claims, has an active effect on the osteo-integration process in vivo, without any further peptide immobilization being required, and that the properties of those devices being implantable by contact to bone tissue having a layer of immobilized hyaluronic acid according to the invention are definitely improved compared to conventional devices.

DESCRIPTION OF THE INVENTION

In the broadest embodiment thereof, the present invention relates to a bone tissue implant device (defined as the "implant device" herein below), of metal or polymer nature, a layer of hyaluronic acid being chemically bound on the surface thereof, such as defined in the annexed claim 1. No limitations have been set to the shape or nature of the device, with the proviso that it is destined to applications providing either the growth of the bone tissue in contact thereto or, generally, the bone tissue growth stimulation.

In a particularly advantageous embodiment of this invention, the device consists of a dental implant screw, preferably made of titanium or alloys thereof, or a screw, preferably made of titanium or alloys thereof, for spinal or skeletal fixation, or of an intervertebral disc, preferably made of titanium, alloys thereof or cobalt-chromium alloys or metal alloys commonly used with this applications, or a cage, preferably made of titanium or alloys thereof.

A thin layer of hyaluronic acid, preferably 0.5 to 10000 nm, more preferably 1 to 1000 nm, still more preferably 1.5 to 100 nm, is immobilized on the surface of these alloys.

The process of immobilizing hyaluronic acid on an implant device according to the invention provides the introduction of amine functional groups on the surface of the device and the consequent bond of hyaluronic acid to said amine groups by means of functionalization of the hyaluronic acid hydroxyl groups. The hyaluronic acid is in fact a mucopolysaccharide of a molecular weight comprised between 50.000 and 8.000.000, wherein there are present repeats of the formula:

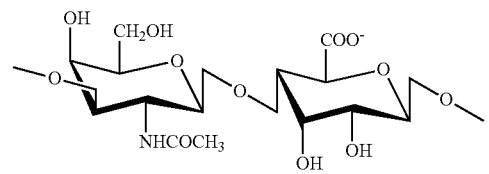

containing easily functionalizable primary alcohol groups.

Accordingly, an object of the present invention is an implant device comprising a substrate coating having amine groups, wherein hyaluronic acid is bound to said substrate by functionalization of hydroxyl groups of said hyaluronic acid.

The substrate containing the amine groups can be laid on the surface of the implant device according to methods widely known in the field. The technique providing the introduction of the substrate having amine functional groups on the surface of the implant device by means of plasma deposition of molecules containing amine groups is particularly advantageous. Typical examples of molecules being used to the purpose are allylamine, alkylamine such as hexyl- or heptyl-amine and, generally, the organic molecules with amine functionality having the required characteristics of volatility in the plasma phase. The plasma deposition of amine is carried out in the following conditions: pressure comprised between 80 and 300 mTorr, input power comprised between 5 and 200 W, deposition time comprised between 1 ms and 300 s. The plasma deposition can also take place in conditions of pulsed plasma, with cycles of active and inactive plasma comprised between 1 and 100 ms, to minimize the molecular fragmentation and maintain the greatest possible density of amine groups. The treatment of plasma deposition of amine can be preceded by other treatments by plasma, for example air or oxygen plasma to clean the surface and increase the adhesion to the substrate.

The hyaluronic acid can be bound to the amine layer by aqueous or suitable solvent solution such as dimethylsulphoxide or mixture thereof with water, dimethylformamide or mixtures thereof with water, N-methylpyrrolidone or mixtures thereof with water, by the methods known in the art for the functionalization of hydroxyl groups and particularly for the substitution of a hydroxyl group with an amine-type bond:

wherein Ial is the residue of hyaluronic acid and Sub is the residue of the substrate having amine functionalities. From what has been stated above, it is understood that the process of the invention can provide the functionalization of all reactive hydroxyl groups of hyaluronic acid as well as only some of them, according to the reaction being employed and the reaction conditions being applied from case to case. However, it is necessary and sufficient that the functionalization reaction of the hydroxyl groups of the hyaluronic acid leads to the formation of a hyaluronic acid layer being bound with a fractional coverage, i.e. the surface portion covered by hyaluronic acid, greater than 0.6, as evaluated by means of the X-ray Photoelectron Spectroscopy, known by the acronym XPS or ESCA. The testing method is reported in the article by Marco Morra and Clara Cassinelli: "Simple model for the XPS analysis of polysaccharide-coated surfaces", issued on the Surface and Interface Analysis magazine, 26, 742-746 (1998).

The functionalization reaction of the hydroxyl groups of the hyaluronic acid with the amine of the substrate can be carried out according to various methods known to those skilled in the art, such as the following (being listed by way of non-exhaustive examples):

- activation of the hydroxyl group by formation of mesylates, tosylates or similar leaving groups, for example by reaction of the hyaluronic acid with mesyl or tosyl chloride, and the subsequent reaction of the activated hydroxyl groups with the amine;
- substitution of the hydroxyl group with a halo, such as chlorine, bromine or iodine, for example by reaction of the hyaluronic acid with thyonil chloride or carbon tetrabromide and triphenylphospine, and a subsequent reaction of the halogenated hyaluronic acid with the amine;
- Mitsunobu reaction of the hyaluronic acid with amine, in the presence of diethylazadicarboxylate and triphenylphospine;
- oxidation of primary hydroxyl groups to aldehydes and subsequent reductive amination.

Among the methods cited above, the synthetic pathway providing the oxidation of hydroxyl groups of the hyaluronic acid to aldehyde and subsequent reductive amination of the thus-formed aldehyde is to be preferred.

The oxidation reaction of the primary alcohol group to aldehyde can be carried out by using any selective oxidation agent of an alcohol group, such as chromium trioxide or sodium or potassium periodate. Sodium periodate is the preferred reagent in this reaction.

The thus formed aldehyde groups react with the amine groups of the alkyl- or allyl-amine by reductive amination in the presence of a suitable reduction agent, such as by way of non-limiting example: hydrogen in the presence of a suitable catalyzer such as Raney nickel or $PtO_2$; aluminum, aluminum amalgam or $Al/HgCl_2$; boranes such as decaborane; sodium cyanoborohydride or a borohydride immobilized on resin for solid phase synthesis, such as MP-cyanoborohydride, MP-triacetoxyborohydride in the presence of a suitable scavenger such as for example PS-isocyanate, PS-benzaldehyde or MP-TsOH.

A preferred reagent for the reductive amination is sodium cyanoborohydride.

The reaction conditions employed for the oxidation of the hydroxyl group to aldehyde and for the reductive amination of the aldehyde are those normally employed in this type of reactions, such as exemplified in the experimental section below.

The advantage of functionalizing the hydroxyl groups of the hyaluronic acid instead of the carboxyl groups is that this method allows to leave the carboxyl groups fully available for interaction with calcium ions, thereby maximizing the hyaluronic acid activity of promotion of the bone mineralization.

According to a preferred embodiment of the invention, besides the bound hyaluronic acid layer, the implant device can comprise releasable drugs or bioactive agents that are capable of promoting the growth of bone tissue. In this embodiment, the device will be first coated preferably with a polymer or ceramic layer that is capable of englobing, absorbing or adsorbing the drug or bioactive ingredient, on which layer the hyaluronic acid will be then immobilized according to the techniques described above.

Among the drugs or bioactive principles being employed in accordance with the present invention, particularly favoured are those playing a role as bone growth stimulators. Among them, the dexamethasone drug, the dexamethasone-phosphate or acetate soluble form thereof, the vitamin D in the various forms thereof, growth factors, the family of proteins known as the bone morphogenetic proteins, molecules of the polysaccharide type such as eparine, condroitin sulphate and hyaluronic acid are particularly preferred.

Besides the absence of inherent toxicity, there is no chemical limit to the nature of the layer englobing the drug or bioactive ingredient, the composition thereof may be adapted to the characteristics of the drug or bioactive principle and the desired kinetic release. Non-exhaustive examples are polymers of silicone, olefine, acrylic type such as polymethyldisiloxane, polybutadiene polymethylmethacrylate, polyethylmethacrylate, polybutylmethacrylate, poliuretanes, fluorinated polymers, polyesthers, hydrophilic acrylates such as poly-hydroxyethylmetacrilate or poly-hydroxybutylmethacrilate; the optional ceramic layer may consist of alumine- or silicate- or silico-aluminate-based inert ceramics, or bioactive ceramics such as calcium phosphates or hydroxyapatite. This layer may be either in compact or porous form, according to what is required by the release kinetic control.

The polymer or ceramic layers may be deposited according to the conventional techniques, by immersion, spraying, both by conventional spray gun and ultrasound spraying, by vapour-phase or plasma deposition. In the case of ceramic layers, the sol-gel technique may as well be used.

The drug or active ingredient will be deposited, englobed, absorbed or adsorbed in the support layer according to conventional techniques, such as spraying from common solutions, suspensions, emulsions, or by common processes of immersion in solution, suspensions, emulsions.

Within the spirit of the present invention, the layer englobing the drug or active ingredient will be in turn modified by depositing a substrate carrying amine groups and subsequent covalent bond of hyaluronic acid to said substrate, according to the scheme described above. For example, after having applied the layer englobing the drug or active ingredient, there is carried out a process of plasma deposition of allylamine or alkylamine, hyaluronic acid in aqueous solution being then bound thereto. The optional release and loss of drug in this step, will be balanced by an initial measured overdose, by englobing an excess of drug or bioactive ingredient in the polymer or ceramic matrix. This excess will be generally up to 30% of the stoichiometrical amount, more preferably up to 10% of the stoichiometrical amount.

As will be understood from the experimental tests reported herein below, it has been surprisingly found that, contrary to what would have been expected according to the literature data, the hyaluronic acid immobilized on an implant device implanted in the bone carries out a marked osteointegrative action. It is therefore a further object of the present invention to use the hyaluronic acid for preparing a bone-contact implant device, wherein said hyaluronic acid is immobilized on the surface of said implant device, such as the promoting agent of osteo-integration.

EXPERIMENTAL SECTION

Example 1

Titanium Samples with a Layer of Immobilized Hyaluronic Acid

Three 99.7% titanium samples (Sigma-Aldrich), in the shape of 1 cm-side squares, are subjected to a process of plasma deposition of allylamine, by using a Gambetti Kenologia reactor for plasma treatment. Particularly, the deposition process is carried out by pulsed plasma, using 10 ms cycles, at 100 mTorr pressure. Input power is 50 W, treatment time is 30 s. At the end of the treatment, the screw is immersed in a pre-treated hyaluronic acid solution, at 0.5% water concentration. The hyaluronic acid is manufactured by Lifecore Biomedical, Chaska, Minn., USA and is identified by the batch n. B22157. The hyaluronic acid aqueous solution had been pre-treated for 16 hours in phosphate buffer with sodium periodate (16 mg/100 cc) and mixed, upon the reaction, with an equal volume of acetic buffer containing 1 mg/cc sodium cyanoborohydride. The samples are maintained in the solution overnight, then washed with water and dried under a laminar flux hood.

Example 2

Evaluation of the Cell Non-Adesivity of the Samples

The three samples from example 1, together with three similarly sized samples of non-modified titanium are subjected to cell adhesion tests with cells of the osteoblastic type (MG-63), being supplied by the Brescia Institute of Zooprophylaxis. The cells, being cultured according to the traditional methods, are seeded on two samples modified with hyaluronic acid and two controls consisting of non-modified titanium. After a 3-day culture, the samples are delicately washed with phosphate buffer, the adhered cells are removed with tripsine and counted with a hemocytometer. The following results are obtained:

| Sample | No. of cells (mean and standard deviation) |
|---|---|
| Control | $3.4 \times 10^6 \pm 1.1 \times 10^5$ |
| HA coated | $1.1 \times 10^3 \pm 0.8 \times 10^3$ |

The data confirms the considerable reduction of the number of cells present on the surface being modified by hyaluronic acid, in accordance with the literature data being cited above.

Example 3

Titanium Screws with Immobilized Hyaluronic Acid Layer

The experiment of example 1 is repeated on a titanium implant screw manufactured by Agliati s.r.l. The screw is tested by X-ray Photoelectron Spectroscopy (XPS), a surface testing technique capable of providing the chemical composition of a surface layer of the material up to approximately 8 nm depth. The following results are obtained (data is expressed in atomic %):

| C | O | N | Other < 1% |
|---|---|---|---|
| 70.5 | 18.1 | 10.1 | Si, S, P |

The observed stoichiometry, particularly the presence of nitrogen and the C/O and C/N ratios, is consistent with the presence of a thin surface layer of hyaluronic acid, such as expected by the typology of binding reaction and in accordance with the literature data.

Example 4

Confirmation In Vivo of the Improved Osteo-Integration Characteristics

To evaluate the characteristics in vivo of the titanium implantable devices obtained according to the invention, several tests on rabbits are carried out. Particularly, screws of 2 mm diameter and 10 mm length are implanted in the cortical bone of the femoral diaphysis of 10 adult rabbits, for a total of 10 coated screws and 10 uncoated controls. The animals are sacrificed after four weeks and the femurs are prepared for histological examination and mechanical tests. Particularly, the measured parameters are:

the affinity index, i.e. the ratio of bone length directly opposite the interface, without the intervention of fibrous tissue, and the total length of the interface, multiplicated by 100.

the bone growth, i.e. the percentage ratio of the bone-filled area and the total area enclosed between the screw and the vertexes of a spire, such as observed in the histological examination section.

Furthermore, by means of a pull out test machine, the maximum force required to extract the screw from the bone is measured (Pull Out force).

The following results are obtained:

| | | Screw | |
|---|---|---|---|
| Parameter | | Uncoated | Coated with hyaluronic acid |
| Affinity index (%) | Mean | 55.0 | 69.7 |
| | Standard deviation | 5.2 | 2.9 |
| | (Min-Max) | (42.7-66.9) | (62.3-80.3) |
| Bone growth (%) | Mean | 84.5 | 91.0 |
| | Standard deviation SEM | 3.3 | 0.7 |
| | (Min-Max) | (70.1-88.8) | (89.7-93.7) |
| Pull out force (N) | Mean | 185.3 | 232.2 |
| | Standard deviation | 10.7 | 18.4 |
| | (Min-Max) | (130.6-185.6) | (197.3-299.5) |

Both the histomorphometric data and the mechanical tests clearly indicate that the screws coated with hyaluronic acid, implanted in the bone, do not exert the bio-passive and anti-adhesive effect as would have been expected according to the current knowledge on immobilized hyaluronic acid, but they surprisingly have definitely improved osteo-integration characteristics compared to the uncoated screws.

Example 5

Titanium Screw with a Layer for Drug Release and Immobilization of Hyaluronic Acid Thereon Several titanium screws are initially subjected to a process of plasma deposition of propene, by using the reactor described in the example 1. Subsequently, the screws are coated with a thin polymer layer and with dexamethasone, using a spray gun (Conrad-Bartoli), loaded with the following solution:

0.5% polybutylmethacrylate and 0.1% dexamethasone (both supplied by Sigma Aldrich) in a 50-50 mixture of acetone and methyl alcohol.

The screws thus obtained are subjected to the process described in the examples 1 and 3, thereby providing a titanium screw combining the characteristics of releasing a bone growth promoting drug and having a bioactive surface coated with hyaluronic acid.

Example 6

Release of Dexamethasone from a Titanium Device With an Immobilized Layer of Hyaluronic Acid A screw obtained such as described in the example 5 is dipped in 2 cc of saline and maintained in an incubator at 37° C. At given times, the solution is taken off and the UV-Vis absorbance spectrum is measured at 242.4 nm, which is the maximum absorbance wavelength of dexamethasone. The release curve is obtained as a function of the time, as shown in FIG. 1.

The bone tissue implant device thus obtained is then capable of coupling the release of a drug affecting the bone formation process to the bioactivity of the surface coated with hyaluronic acid being described above.

Among the feasible variants that can be provided for the implant device without departing from the scope of the present invention, there are implant devices made of materials other than titanium, alloys thereof or cobalt-chromium, such as for example common stainless steel. This is allowed by the particular osteointegrative effect obtainable with the devices of the present invention.

The invention claimed is:

1. An implant device configured to implant into contact with bone tissue, said implant comprising a bone anchoring portion for implanting into contact with bone tissue, said portion having a coating of a substrate having amine groups; and a layer of hyaluronic acid being chemically bound on surface of said portion to provide a stimulating activity on the growth of bone tissue; wherein hyaluronic acid is bound to said substrate by functionalization of hydroxyl groups of said hyaluronic acid.

2. The implant device according to claim 1, wherein said device is a dental implant screw, a spinal or skeletal fixation screw, an intervertebral disc or a cage.

3. The implant device according to claim 2, wherein said screws and said cage are made of titanium or alloys thereof.

4. The implant device according to claim 2, wherein said intervertebral disc is made of titanium, alloys thereof or cobalt-chromium alloys.

5. The implant device according to claim 4 whose surface topography has been roughened by sandblasting, acid etching or electrochemical treatment.

6. The implant device according to claim 1, wherein said substrate having amine groups comprises allylamine or alkylamine units, preferably selected from hexyl- or heptyl-ammine.

7. The implant device according to claim 1, wherein the layer of said hyaluronic acid has a thickness comprised between 0.5 and 10000 nm.

8. The implant device according to claim 1, wherein the layer of said hyaluronic acid has a thickness comprised between 1 and 1000 nm.

9. The implant device according to claim 1, wherein the layer of said hyaluronic acid has a thickness comprised between 1.5 and 100 nm.

10. The implant device according to claim 1, wherein the layer of said hyaluronic acid has a fractional coverage greater than 0.6, evaluated by means of the X-ray Photoelectron Spectroscopy technique.

11. The implant device according to claim 1, said device further comprising releasable drugs or bioactive agents that are capable of promoting bone tissue growth.

12. The implant device according to claim 11 wherein said drugs or bioactive agents are englobed adsorbed or absorbed in a biodegradable or water soluble layer.

13. The implant device according to claim 12 wherein said biodegradable layer is made of hyaluronic acid, cross-linked hyaluronic acid or hyaluronic acid derivatives such as total hyaluronic acid esters.

14. The implant device according to claim 11, wherein said drugs or bioactive agents are either englobed, absorbed or adsorbed on a polymer or ceramic layer.

15. The implant device according to claim 14, wherein said substrate on which the hyaluronic acid is immobilized is deposited on said polymer or ceramic layer in which said drug or bioactive ingredient is either englobed, absorbed or adsorbed.

16. The implant device according to claim 14, wherein said polymer substrate comprises polymers of the silicone, olefine or acrylic type, which are preferably selected from polymethyldisiloxane, polybutadiene, polymethylmethacrylate, polyethylmethacrylate, polybutylmethacrylate, poliuretanes, fluorinated polymers, polyesthers, hydrophilic polyacrylates preferably selected from poly-hydroxyethylmetacrilate or polyhydroxybutylmethacrilate.

17. The implant device according to claim 14, wherein said ceramic layer comprises allumina-, silicate-, or silico-aluminate-based inert ceramics, or bioactive ceramics such as calcium phosphates or hydroxyapatite.

18. The implant device according to claim 14, wherein said ceramic layer is in the compact or porous form.

19. The implant device according to claim 11, wherein said drug or bioactive drug is selected from dexamethasone, the dexamethasone-phosphate or acetate soluble forms thereof, the vitamine D in the various forms thereof, growth factors, the family of proteins known as the bone morphogenetic proteins, molecules of the polysaccharide type such as eparine, condroitin sulphate and hyaluronic acid.

20. The implant device according to claim 1, obtained by means of a process comprising the steps of:
providing a metal or polymer implant device having a bone anchoring portion for implanting into contact with bone tissue;
coating the surface of said anchoring portion of said implant device with a substrate having amine groups;
binding hyaluronic acid to the amine groups of said substrate by functionalization of hydroxyl groups of said hyaluronic acid.

* * * * *